United States Patent [19]

Levitt

[11] Patent Number: 4,668,281

[45] Date of Patent: May 26, 1987

[54] THIOPHENESULFONAMIDES

[75] Inventor: George Levitt, Wilmington, Del.

[73] Assignee: E. I. Du Pont de Nemours and Company, Wilmington, Del.

[21] Appl. No.: 849,332

[22] Filed: Apr. 10, 1986

Related U.S. Application Data

[63] Continuation-in-part of Ser. No. 735,529, May 20, 1985, abandoned.

[51] Int. Cl.⁴ .................. C07D 251/42; C07D 251/16; A01N 43/66
[52] U.S. Cl. ........................................ 71/93; 544/113; 544/212
[58] Field of Search ........................... 544/212; 71/93; 544/113

[56] References Cited

U.S. PATENT DOCUMENTS 4,501,607 2/1985 Levitt ................................. 544/212
4,515,626 5/1985 Szczepanski ....................... 544/211
4,547,217 10/1986 Shapiro ............................. 544/212
4,589,909 5/1986 Rorer ................................. 544/212

Primary Examiner—John M. Ford

[57] ABSTRACT

Thiophenesulfonamides useful as herbicides and plant growth regulants, herbicidal compositions containing thiophenesulfonamides, and methods of applying the compositions to areas containing undesired vegetation are described.

9 Claims, No Drawings

THIOPHENESULFONAMIDES

SUMMARY OF THE INVENTION

This invention relates to novel compounds of the formula:

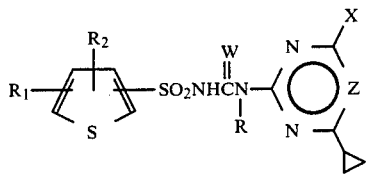

I wherein
W is O or S;
R is H or $CH_3$
$R_1$ is H, $C_1$-$C_4$ alkyl, $CH_2CH=CH_2$, $CF=CFCF_3$, $C_1$-$C_2$ alkoxy, $NO_2$, Cl, Br, $SO_2NR_3R_4$, $SO_2N(OCH_3)CH_3$, $S(O)_nR_5$, $CO_2R_6$, $C(O)NR_7R_8$, $C(O)R_9$ or $C_1$-$C_2$ alkyl substituted with F, Cl, $C_1$-$C_2$ alkoxy, $C_1$-$C_2$ alkylthio or CN;
$R_2$ is H, Cl, F, Br, $C_1$-$C_2$ alkyl, $C_1$-$C_2$ alkoxy, $S(O)_nR_{10}$, $C_1$-$C_2$ haloalkyl, CN, $C_2$-$C_3$ cyanoalkyl, $CH_2OCH_3$, $CH_2SCH_3$ or $CH_2CH_2OCH_3$;
$R_3$ and $R_4$ are independently $C_1$-$C_3$ alkyl;
$R_3$ and $R_4$ may be taken together as $(CH_2)_4$, $(CH_2)_5$ or $CH_2CH_2OCH_2CH_2$;
$R_5$ is $C_1$-$C_3$ alkyl or $CH_2CH=CH_2$;
$R_6$ is $C_1$-$C_3$ alkyl, $CH_2CH=CH_2$, $CH_2C\equiv CH$, $CH_2CH_2Cl$ or $CH_2CH_2OCH_3$;
$R_7$ is $C_1$-$C_3$ alkyl;
$R_8$ is H, $C_1$-$C_3$ alkyl or $CH_2CH=CH_2$;
$R_9$ is H or $C_1$-$C_3$ alkyl;
$R_{10}$ is $C_1$-$C_2$ alkyl;
n is 0, 1 or 2;
X is $CH_3$, $OCH_3$, $OCH_2CH_3$, $CH_2OCH_3$ or $OCF_2H$; and
Z is CH or N;
and their agriculturally suitable salts; provided that $R_1$ and the sulfonylurea bridge are on adjacent carbon atoms of the thiophene ring and also provided that when X is $OCF_2H$ then Z is CH.

Preferred for reasons of their higher herbicidal activity, greater plant growth regulant activity or more favorable ease of synthesis are:
(1) Compounds of Formula I wherein
W is O;
R is H;
$R_1$ is H, $C_1$-$C_2$ alkyl, $CF=CFCF_3$, Cl, Br, $SO_2N(CH_3)_2$, $SO_2(C_1$-$C_2$ alkyl) or $CO_2(C_1$-$C_2$ alkyl);
$R_2$ is H, F, Br, Cl, $CH_3$, $S(O)_nCH_3$, or $CH_2OCH_3$; and
X is $CH_3$ or $OCH_3$.

Specifically Preferred for reasons of greatest ease of synthesis and/or greatest herbicidal efficacy is:
3-[[(4-cyclopropane-6-methoxy-1,3,5-triazin-2-yl)aminocarbonyl]aminosulfonyl]-2-thiophenecarboxylic acid, methyl ester.

DETAILED DESCRIPTION OF THE INVENTION

The compounds of Formula I can be prepared in an inert organic solvent by one of several processes.
According to one process, the compounds of Formula I are produced by reacting a sulfonamide of Formula II, wherein $R_1$ and $R_2$ are as previously defined, and an N-pyrimidinyl- or N-triazinylcarbamate of Formula III, wherein W, X and Z have the meanings defined under Formula I, and B—O— is a phenoxy or alkoxy group which can be displaced as illustrated in Equation (1).

Equation (1)

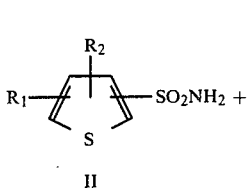

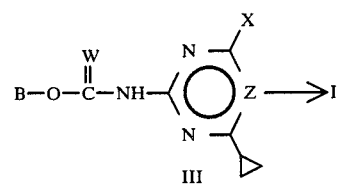

According to a second process, compounds of Formula I are produced by reacting a sulfonyl isocyanate or sulfonyl isothiocyanate of Formula IV, wherein $R_1$, $R_2$ and W are as previously defined, in the presence or absence of a base, with an amine of Formula V, wherein R, X and Z have the meanings defined under Formula I, illustrated in Equation (2).

Equation (2)

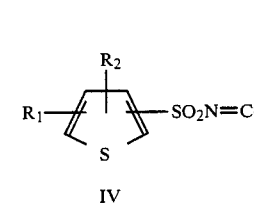

According to a further process, illustrated in Equation (3), compounds of Formula I can be prepared by reacting a sulfonamide of Formula II given above, in the presence or absence of a base, with an isocyanate or isothiocyanate of Formula VI wherein W, X and Z are as previously defined.

Equation (3)

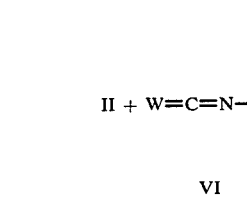

Furthermore, compounds of Formula I can be produced by reacting an N-thiophenesulfonylcarbamate of Formula VII, illustrated in Equation (4), wherein $R_1$, $R_2$ and B have the meanings defined above, with an amine of Formula V.

Equation (4)

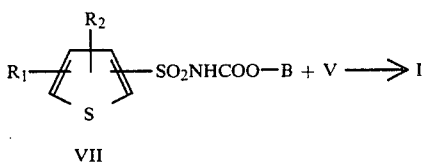

VII

The resulting ureas of Formula I can, if required, be converted by means of amines, alkali metal hydroxides or alkaline-earth metal hydroxides or quaternary ammonium bases, into addition salts. This is effected, for example, by reaction with an equimolar amount of a base, and removal of the solvent by evaporation.

The starting materials of the Formulae II, IV and VII are, in many cases, known or can be prepared by one skilled in the art according to methods described in U.S. Pat. Nos. 4,127,405; 4,398,939; 4,481,910; and 4,481,029, the disclosures of which are incorporated herein by reference.

The cyclopropylpyrimidines and cyclopropyltriazines of Formula V, to which the intermediates of Formulae III and VI are closely related, are also known and can be produced by one skilled in the art according to methods described in U.S. Pat. No. 4,515,626.

The selection of the appropriate process for the production of compounds of Formula I is dependent in part on the relative reactivities and syntheses of compounds of Formulae II–VII. Such decisions are obvious to one skilled in the art.

The following Example sets forth the invention in greater detail.

EXAMPLE 1

Methyl 3-[[[(4-cyclopropane-6-methoxy-1,3,5-triazine-2-yl)aminocarbonyl]aminosulfonyl]]thiophene-2-carboxylate To 0.8 g of 2-amino-4-cyclopropyl-6-methoxy-1,3,5-triazine in 35 mL of dry methylene chloride was added methyl 3-isocyanatosulfonylthiophene-2-carboxylate. After being stirred at reflux for one-half hour, the mixture was cooled in an ice-acetone bath and the precipitate removed by filtration. Evaporation of the filtrate yielded a residue which was washed with a small amount of acetonitrile to yield 0.3 g of a solid. This product, m.p. 142°–169° C., showed absorption peaks by infrared spectroscopy at 1730, 1720, 1600 and 1550 cm$^{-1}$, consistent with the desired structure.

NMR(CDCl$_3$): δ 3.85 (s, CH$_3$O on triazine) 4.05 (s, CH$_3$O ester) 0.8–1.5 (m, cyclopropyl) 7.7–7.9 (m, thiophene)

This product was sufficiently pure for the purposes of this invention.

Following the procedures described earlier and exemplified in the Example, one skilled in the art can prepare the compounds of Tables I, II and III.

General Structure for Table I

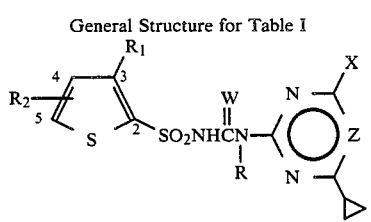

General Structure for Table II

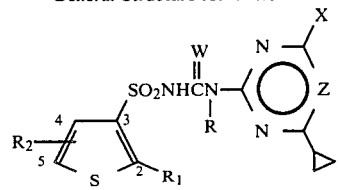

General Structure for Table III

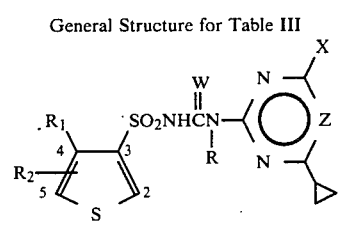

TABLE I

General Structure I

| R | R$_1$ | R$_2$ | W | X | Z | m.p. (°C.) |
|---|---|---|---|---|---|---|
| H | H | H | O | CH$_3$ | CH | |
| H | H | H | O | OCH$_3$ | CH | |
| H | H | H | O | CH$_3$ | N | |
| H | H | H | O | OCH$_3$ | N | |
| H | Cl | H | O | CH$_3$ | CH | |
| H | Cl | H | O | OCH$_3$ | CH | |
| H | Cl | H | O | CH$_3$ | N | |
| H | Cl | H | O | OCH$_3$ | N | |
| H | Br | H | O | CH$_3$ | CH | |
| H | Br | H | O | OCH$_3$ | CH | |
| H | Br | H | O | CH$_3$ | N | |
| H | Br | H | O | OCH$_3$ | N | |
| H | CH$_3$ | H | O | CH$_3$ | CH | |
| H | CH$_3$ | H | O | OCH$_3$ | CH | |
| H | CH$_3$ | H | O | CH$_3$ | N | |
| H | CH$_3$ | H | O | OCH$_3$ | N | |
| H | CH$_2$CH$_3$ | H | O | CH$_3$ | CH | |
| H | CH$_2$CH$_3$ | H | O | OCH$_3$ | CH | |
| H | CH$_2$CH$_3$ | H | O | CH$_3$ | N | |
| H | CH$_2$CH$_3$ | H | O | OCH$_3$ | N | |
| CH$_3$ | CH$_2$CH$_2$CH$_3$ | H | O | CH$_3$ | CH | |
| H | CH$_2$CH$_2$CH$_2$CH$_3$ | 5-Cl | O | OCH$_3$ | CH | |
| H | CH$_2$CH=CH$_2$ | H | S | CH$_3$ | N | |
| H | CF=CFCF$_3$ | H | O | CH$_3$ | CH | |
| H | CF=CFCF$_3$ | H | O | OCH$_3$ | CH | |
| H | CF=CFCF$_3$ | H | O | CH$_3$ | N | |
| H | CF=CFCF$_3$ | H | O | OCH$_3$ | N | |
| H | OCH$_3$ | H | O | OCH$_2$CH$_3$ | N | |
| H | OCH$_2$CH$_3$ | H | O | CH$_2$OCH$_3$ | CH | |
| H | NO$_2$ | H | O | OCF$_2$H | CH | |
| H | SO$_2$N(CH$_3$)$_2$ | H | O | CH$_3$ | CH | |
| H | SO$_2$N(CH$_3$)$_2$ | H | O | OCH$_3$ | CH | |
| H | SO$_2$N(CH$_3$)$_2$ | H | O | CH$_3$ | N | |
| H | SO$_2$N(CH$_3$)$_2$ | H | O | OCH$_3$ | N | |
| H | SO$_2$N(CH$_3$)(CH$_2$CH$_3$) | 5-CH$_3$ | O | CH$_3$ | CH | |
| H | SO$_2$N(CH$_3$)(CH$_2$CH$_2$CH$_3$) | H | O | OCH$_3$ | CH | |
| H | SO$_2$N(CH$_2$CH$_3$)$_2$ | H | O | CH$_3$ | N | |
| H | SO$_2$N(CH$_2$CH$_2$CH$_3$)$_2$ | H | O | OCH$_3$ | N | |
| H | SO$_2$N(OCH$_3$)CH$_3$ | H | O | CH$_3$ | CH | |
| H | SCH$_3$ | H | O | OCH$_3$ | CH | |
| H | SCH$_2$CH$_3$ | H | O | CH$_3$ | N | |
| H | SCH$_2$CH$_2$CH$_3$ | H | O | OCH$_3$ | N | |
| H | SCH$_2$CH=CH$_2$ | H | O | CH$_3$ | CH | |
| H | S(O)CH$_3$ | 4-Cl | O | OCH$_3$ | CH | |
| H | S(O)CH$_2$CH$_3$ | H | O | CH$_3$ | N | |
| H | S(O)CH$_2$CH$_2$CH$_3$ | H | O | OCH$_3$ | N | |
| H | S(O)CH$_2$CH=CH$_2$ | H | O | CH$_3$ | CH | |
| H | SO$_2$CH$_3$ | H | O | CH$_3$ | CH | |
| H | SO$_2$CH$_3$ | H | O | OCH$_3$ | CH | |
| H | SO$_2$CH$_3$ | H | O | CH$_3$ | N | |
| H | SO$_2$CH$_3$ | H | O | OCH$_3$ | N | |
| H | SO$_2$CH$_2$CH$_3$ | H | O | CH$_3$ | CH | |
| H | SO$_2$CH$_2$CH$_3$ | H | O | OCH$_3$ | CH | |
| H | SO$_2$CH$_2$CH$_3$ | H | O | CH$_3$ | N | |
| H | SO$_2$CH$_2$CH$_3$ | H | O | OCH$_3$ | N | |

TABLE I-continued

General Structure I

| R | R₁ | R₂ | W | X | Z | m.p. (°C.) |
|---|---|---|---|---|---|---|
| H | SO₂CH₂CH₂CH₃ | H | O | CH₃ | CH | |
| H | SO₂CH₂CH=CH₂ | H | O | OCH₃ | CH | |
| H | CO₂CH₃ | H | O | CH₃ | CH | |
| H | CO₂CH₃ | H | O | OCH₃ | CH | |
| H | CO₂CH₃ | H | O | CH₃ | N | |
| H | CO₂CH₃ | H | O | OCH₃ | N | |
| H | CO₂CH₂CH₃ | H | O | CH₃ | CH | |
| H | CO₂CH₂CH₃ | H | O | OCH₃ | CH | |
| H | CO₂CH₂CH₃ | H | O | CH₃ | N | |
| H | CO₂CH₂CH₃ | H | O | OCH₃ | N | |
| H | CO₂CH₂CH₂CH₃ | H | O | CH₃ | CH | |
| H | CO₂CH(CH₃)₂ | 4-CH₃ | O | OCH₃ | CH | |
| H | CO₂CH₂CH=CH₂ | H | O | CH₃ | N | |
| H | CO₂CH₂C≡CH | H | O | OCH₃ | N | |
| H | CO₂CH₂CH₂Cl | H | O | CH₃ | CH | |
| H | CO₂CH₂CH₂OCH₃ | H | O | OCH₃ | CH | |
| H | CONHCH₃ | H | O | CH₃ | N | |
| H | CON(CH₃)CH₂CH₃ | H | O | OCH₃ | N | |
| H | CON(CH₃)₂ | H | O | CH₃ | CH | |
| H | CON(CH₂CH₂CH₃)(CH₃) | H | O | OCH₃ | CH | |
| H | CON(CH₂CH=CH₂)(CH₃) | H | O | CH₃ | N | |
| H | CHO | H | O | OCH₃ | N | |
| H | C(O)CH₃ | H | O | CH₃ | CH | |
| H | C(O)CH₂CH₃ | H | O | OCH₃ | N | |
| H | C(O)CH₂CH₂CH₃ | H | O | CH₃ | CH | |
| H | CF₂H | H | O | OCH₃ | CH | |
| H | CH₂CH₂F | H | O | CH₃ | N | |
| H | CCl₃ | H | O | OCH₃ | N | |
| H | CHClCH₂Cl | H | O | CH₃ | CH | |
| H | CH₂OCH₃ | H | O | OCH₃ | CH | |
| H | CH₂CH₂OCH₂CH₃ | H | O | CH₃ | N | |
| H | CH₂SCH₂CH₃ | H | O | OCH₃ | N | |
| H | CH₂CH₂SCH₃ | H | O | CH₃ | CH | |
| H | CH₂CN | H | O | OCH₃ | CH | |
| H | CH₂CH₂CN | H | O | CH₃ | N | |
| H | C(O)N(pyrrolidine) | H | O | CH₃ | CH | |
| H | C(O)N(pyrrolidine) | H | O | OCH₃ | CH | |
| H | C(O)N(pyrrolidine) | H | O | CH₃ | N | |
| H | C(O)N(pyrrolidine) | H | O | OCH₃ | N | |
| H | C(O)N(piperidine) | H | O | CH₃ | CH | |
| H | C(O)N(piperidine) | H | O | OCH₃ | CH | |
| H | C(O)N(piperidine) | H | O | CH₃ | N | |
| H | C(O)N(piperidine) | H | O | OCH₃ | N | |
| H | C(O)N(morpholine) | H | O | CH₃ | CH | |
| H | C(O)N(morpholine) | H | O | OCH₃ | CH | |
| H | C(O)N(morpholine) | H | O | CH₃ | N | |
| H | C(O)N(morpholine) | H | O | OCH₃ | N | |
| H | CO₂CH₃ | H | O | OCH₂CH₃ | CH | |
| H | CO₂CH₃ | H | O | CH₂OCH₃ | CH | |
| H | CO₂CH₃ | H | O | OCF₂H | CH | |
| H | CO₂CH₃ | H | O | OCH₂CH₃ | N | |
| H | CO₂CH₃ | H | O | CH₂OCH₃ | N | |
| H | CO₂CH₃ | 5-CH₃ | O | CH₃ | CH | |
| H | CO₂CH₃ | 5-CH₃ | O | OCH₃ | CH | |
| H | CO₂CH₃ | 5-CH₃ | O | CH₃ | N | |
| H | CO₂CH₃ | 5-CH₃ | O | OCH₃ | N | |
| H | C(O)N(pyrrolidine) | H | O | CH₃ | CH | |
| H | C(O)N(pyrrolidine) | H | O | OCH₃ | CH | |
| H | C(O)N(pyrrolidine) | H | O | CH₃ | N | |
| H | C(O)N(pyrrolidine) | H | O | OCH₃ | N | |
| H | C(O)N(piperidine) | H | O | CH₃ | CH | |
| H | C(O)N(piperidine) | H | O | OCH₃ | CH | |

TABLE I-continued

General Structure I

| R | R₁ | R₂ | W | X | Z | m.p. (°C.) |
|---|---|---|---|---|---|---|
| H | C(O)N-piperidinyl | H | O | CH₃ | N | |
| H | C(O)N-piperidinyl | H | O | OCH₃ | N | |
| H | C(O)N-morpholinyl | H | O | CH₃ | CH | |
| H | C(O)N-morpholinyl | H | O | OCH₃ | CH | |
| H | C(O)N-morpholinyl | H | O | CH₃ | N | |
| H | C(O)N-morpholinyl | H | O | OCH₃ | N | |
| H | CO₂CH₃ | H | O | OCH₂CH₃ | CH | |
| H | CO₂CH₃ | H | O | CH₂OCH₃ | CH | |
| H | CO₂CH₃ | H | O | OCF₂H | CH | |
| H | CO₂CH₃ | H | O | OCH₂CH₃ | N | |
| H | CO₂CH₃ | H | O | CH₂OCH₃ | N | |
| H | CO₂CH₃ | 4-CH₃ | O | CH₃ | CH | |
| H | CO₂CH₃ | 4-CH₃ | O | OCH₃ | CH | |
| H | CO₂CH₃ | 4-CH₃ | O | CH₃ | N | |
| H | CO₂CH₃ | 4-CH₃ | O | OCH₃ | N | |
| H | CO₂CH₃ | 4-Br | O | OCH₃ | N | |
| H | CO₂CH₃ | 4-Br | O | CH₃ | N | |
| H | CO₂CH₃ | 4-Br | O | OCH₃ | CH | |
| H | CO₂CH₃ | 4-Br | O | CH₃ | CH | |

TABLE II

General Structure II

| R | R₁ | R₂ | W | X | Z | m.p. (°C.) |
|---|---|---|---|---|---|---|
| H | H | H | O | CH₃ | CH | |
| H | H | H | O | OCH₃ | CH | |
| H | H | H | O | CH₃ | N | |
| H | H | H | O | OCH₃ | N | |
| H | Cl | H | O | CH₃ | CH | |
| H | Cl | H | O | OCH₃ | CH | |
| H | Cl | H | O | CH₃ | N | |
| H | Cl | H | O | OCH₃ | N | |
| H | Br | H | O | CH₃ | CH | |
| H | Br | H | O | OCH₃ | CH | |
| H | Br | H | O | CH₃ | N | |
| H | Br | H | O | OCH₃ | N | |
| H | CH₃ | H | O | CH₃ | CH | |
| H | CH₃ | H | O | OCH₃ | CH | |
| H | CH₃ | H | O | CH₃ | N | |
| H | CH₃ | H | O | OCH₃ | N | |
| H | CH₂CH₃ | H | O | CH₃ | CH | |
| H | CH₂CH₃ | H | O | OCH₃ | CH | |
| H | CH₂CH₃ | H | O | CH₃ | N | |
| H | CH₂CH₃ | H | O | OCH₃ | N | |
| CH₃ | CH₂CH₂CH₃ | H | O | CH₃ | CH | |
| H | CH₂CH₂CH₂CH₃ | 5-Cl | O | OCH₃ | CH | |
| H | CH₂CH=CH₂ | H | S | CH₃ | N | |
| H | CF=CFCF₃ | H | O | CH₃ | CH | |
| H | CF=CFCF₃ | H | O | OCH₃ | CH | |
| H | CF=CFCF₃ | H | O | CH₃ | N | |
| H | CF=CFCF₃ | H | O | OCH₃ | N | |
| H | OCH₃ | H | O | OCH₂CH₃ | N | |
| H | OCH₂CH₃ | H | O | CH₂OCH₃ | CH | |
| H | NO₂ | H | O | OCF₂H | CH | |
| H | SO₂N(CH₃)₂ | H | O | CH₃ | CH | |
| H | SO₂N(CH₃)₂ | H | O | OCH₃ | CH | |
| H | SO₂N(CH₃)₂ | H | O | CH₃ | N | |
| H | SO₂N(CH₃)₂ | H | O | OCH₃ | N | |
| H | SO₂N(CH₃)(CH₂CH₃) | 5-CH₃ | O | CH₃ | CH | |
| H | SO₂N(CH₃)(CH₂CH₂CH₃) | H | O | OCH₃ | CH | |
| H | SO₂N(CH₂CH₃)₂ | H | O | CH₃ | N | |
| H | SO₂N(CH₂CH₂CH₃)₂ | H | O | OCH₃ | N | |
| H | SO₂N(OCH₃)CH₃ | H | O | CH₃ | CH | |
| H | SCH₃ | H | O | OCH₃ | CH | |
| H | SCH₂CH₃ | H | O | CH₃ | N | |
| H | SCH₂CH₂CH₃ | H | O | OCH₃ | N | |
| H | SCH₂CH=CH₂ | H | O | CH₃ | CH | |
| H | S(O)CH₃ | 4-Cl | O | OCH₃ | CH | |
| H | S(O)CH₂CH₃ | H | O | CH₃ | N | |
| H | S(O)CH₂CH₂CH₃ | H | O | OCH₃ | N | |
| H | S(O)CH₂CH=CH₂ | H | O | CH₃ | CH | |

TABLE II-continued

General Structure II

| R | R$_1$ | R$_2$ | W | X | Z | m.p. (°C.) |
|---|---|---|---|---|---|---|
| H | SO$_2$CH$_3$ | H | O | CH$_3$ | CH | |
| H | SO$_2$CH$_3$ | H | O | OCH$_3$ | CH | |
| H | SO$_2$CH$_3$ | H | O | CH$_3$ | N | |
| H | SO$_2$CH$_3$ | H | O | OCH$_3$ | N | |
| H | SO$_3$CH$_2$CH$_3$ | H | O | CH$_3$ | CH | |
| H | SO$_2$CH$_2$CH$_3$ | H | O | OCH$_3$ | CH | |
| H | SO$_2$CH$_2$CH$_3$ | H | O | CH$_3$ | N | |
| H | SO$_2$CH$_2$CH$_3$ | H | O | OCH$_3$ | N | |
| H | SO$_2$CH$_2$CH$_2$CH$_3$ | H | O | CH$_3$ | CH | |
| H | SO$_2$CH$_2$CH=CH$_2$ | H | O | OCH$_3$ | CH | |
| H | CO$_2$CH$_3$ | H | O | CH$_3$ | CH | |
| H | CO$_2$CH$_3$ | H | O | OCH$_3$ | CH | |
| H | CO$_2$CH$_3$ | H | O | CH$_3$ | N | |
| H | CO$_2$CH$_3$ | H | O | OCH$_3$ | N | 142–169 |
| H | CO$_2$CH$_3$ | 4-CH$_3$ | O | OCH$_3$ | N | 177–179 (d) |
| H | CO$_2$CH$_3$ | 4-CH$_3$ | O | CH$_3$ | N | |
| H | CO$_2$CH$_2$CH$_3$ | H | O | CH$_3$ | CH | 60–62 |
| H | CO$_2$CH$_2$CH$_3$ | H | O | OCH$_3$ | CH | |
| H | CO$_2$CH$_2$CH$_3$ | H | O | CH$_3$ | N | |
| H | CO$_2$CH$_2$CH$_3$ | H | O | OCH$_3$ | N | |
| H | CO$_2$CH$_2$CH$_2$CH$_3$ | H | O | CH$_3$ | CH | |
| H | CO$_2$CH(CH$_3$)$_2$ | 4-CH$_3$ | O | OCH$_3$ | CH | |
| H | CO$_2$CH$_2$CH=CH$_2$ | H | O | CH$_3$ | N | |
| H | CO$_2$CH$_2$C≡CH | H | O | OCH$_3$ | N | |
| H | CO$_2$CH$_2$CH$_2$Cl | H | O | CH$_3$ | CH | |
| H | CO$_2$CH$_2$CH$_2$OCH$_3$ | H | O | OCH$_3$ | CH | |
| H | CONHCH$_3$ | H | O | CH$_3$ | N | |
| H | CON(CH$_3$)CH$_2$CH$_3$ | H | O | OCH$_3$ | N | 134–136 |
| H | CON(CH$_2$CH$_3$)$_2$ | H | O | CH$_3$ | CH | |
| H | CON(CH$_2$CH$_2$CH$_3$)(CH$_3$) | H | O | OCH$_3$ | CH | |
| H | CON(CH$_2$CH=CH$_2$)(CH$_3$) | H | O | CH$_3$ | N | |
| H | CHO | H | O | OCH$_3$ | N | |
| H | C(O)CH$_3$ | H | O | CH$_3$ | CH | |
| H | C(O)CH$_2$CH$_3$ | H | O | OCH$_3$ | N | |
| H | C(O)CH$_2$CH$_2$CH$_3$ | H | O | CH$_3$ | CH | |
| H | CF$_2$H | H | O | OCH$_3$ | CH | |
| H | CH$_2$CH$_2$F | H | O | CH$_3$ | N | |
| H | CCl$_3$ | H | O | OCH$_3$ | N | |
| H | CHClCH$_2$Cl | H | O | CH$_3$ | CH | |
| H | CH$_2$OCH$_3$ | H | O | OCH$_3$ | CH | |
| H | CH$_2$CH$_2$OCH$_2$CH$_3$ | H | O | CH$_3$ | N | |
| H | CH$_2$SCH$_2$CH$_3$ | H | O | OCH$_3$ | N | |
| H | CH$_2$CH$_2$SCH$_3$ | H | O | CH$_3$ | CH | |
| H | CH$_2$CN | H | O | OCH$_3$ | CH | |
| H | CH$_2$CH$_2$CN | H | O | CH$_3$ | N | |
| H | C(O)N(pyrrolidinyl) | H | O | CH$_3$ | CH | |
| H | C(O)N(pyrrolidinyl) | H | O | OCH$_3$ | CH | |
| H | C(O)N(pyrrolidinyl) | H | O | CH$_3$ | N | |
| H | C(O)N(pyrrolidinyl) | H | O | OCH$_3$ | N | 167–169 |
| H | C(O)N(piperidinyl) | H | O | CH$_3$ | CH | |
| H | C(O)N(piperidinyl) | H | O | OCH$_3$ | CH | |

TABLE II-continued

General Structure II

| R | R₁ | R₂ | W | X | Z | m.p. (°C.) |
|---|---|---|---|---|---|---|
| H | piperidine-N-C(=O) | H | O | CH₃ | N | |
| H | piperidine-N-C(=O) | H | O | OCH₃ | N | |
| H | morpholine-N-C(=O) | H | O | CH₃ | CH | |
| H | morpholine-N-C(=O) | H | O | OCH₃ | CH | |
| H | morpholine-N-C(=O) | H | O | CH₃ | N | |
| H | morpholine-N-C(=O) | H | O | OCH₃ | N | |
| H | CO₂CH₃ | H | O | OCH₂CH₃ | CH | |
| H | CO₂CH₃ | H | O | CH₂OCH₃ | CH | |
| H | CO₂CH₃ | H | O | OCF₂H | CH | |
| H | CO₂CH₃ | H | O | OCH₂CH₃ | N | |
| H | CO₂CH₃ | H | O | CH₂OCH₃ | N | |
| H | CO₂CH₃ | 4-CH₃ | O | CH₃ | CH | |
| H | CO₂CH₃ | 4-CH₃ | O | OCH₃ | CH | |
| H | CO₂CH₃ | 4-CH₃ | O | CH₃ | N | |
| H | CO₂CH₃ | 4-CH₃ | O | OCH₃ | N | 177–179 (d) |
| H | CO₂CH₃ | 4-Br | O | CH₃ | N | |
| H | CO₂CH₃ | 4-Br | O | OCH₃ | N | 88–95 |
| H | CO₂CH₃ | 4-Br | O | CH₃ | CH | |
| H | CO₂CH₃ | 4-Br | O | OCH₃ | CH | |

TABLE III

General Structure III

| R | R₁ | R₂ | W | X | Z | m.p. (°C.) |
|---|---|---|---|---|---|---|
| H | H | H | O | CH₃ | CH | |
| H | H | H | O | OCH₃ | CH | |
| H | H | H | O | CH₃ | N | |
| H | H | H | O | OCH₃ | N | |
| H | Cl | H | O | CH₃ | CH | |
| H | Cl | H | O | OCH₃ | CH | |
| H | Cl | H | O | CH₃ | N | |
| H | Cl | H | O | OCH₃ | N | |
| H | Br | H | O | CH₃ | CH | |
| H | Br | H | O | OCH₃ | CH | |
| H | Br | H | O | CH₃ | N | |
| H | Br | H | O | OCH₃ | N | |
| H | CH₃ | H | O | CH₃ | CH | |
| H | CH₃ | H | O | OCH₃ | CH | |
| H | CH₃ | H | O | CH₃ | N | |
| H | CH₃ | H | O | OCH₃ | N | |
| H | CH₂CH₃ | H | O | CH₃ | CH | |
| H | CH₂CH₃ | H | O | OCH₃ | CH | |
| H | CH₂CH₃ | H | O | CH₃ | N | |
| H | CH₂CH₃ | H | O | OCH₃ | N | |
| CH₃ | CH₂CH₂CH₃ | H | O | CH₃ | CH | |
| H | CH₂CH₂CH₂CH₃ | 5-Cl | O | OCH₃ | CH | |
| H | CH₂CH=CH₂ | H | S | CH₃ | N | |

TABLE III-continued

General Structure III

| R | $R_1$ | $R_2$ | W | X | Z | m.p. (°C.) |
|---|---|---|---|---|---|---|
| H | CF=CFCF$_3$ | H | O | CH$_3$ | CH | |
| H | CF=CFCF$_3$ | H | O | OCH$_3$ | CH | |
| H | CF=CFCF$_3$ | H | O | CH$_3$ | N | |
| H | CF=CFCF$_3$ | H | O | OCH$_3$ | N | |
| H | OCH$_3$ | H | O | OCH$_2$CH$_3$ | N | |
| H | OCH$_2$CH$_3$ | H | O | CH$_2$OCH$_3$ | CH | |
| H | NO$_2$ | H | O | OCF$_2$H | CH | |
| H | SO$_2$N(CH$_3$)$_2$ | H | O | CH$_3$ | CH | |
| H | SO$_2$N(CH$_3$)$_2$ | H | O | OCH$_3$ | CH | |
| H | SO$_2$N(CH$_3$)$_2$ | H | O | CH$_3$ | N | |
| H | SO$_2$N(CH$_3$)$_2$ | H | O | OCH$_3$ | N | |
| H | SO$_2$N(CH$_3$)(CH$_2$CH$_3$) | 5-CH$_3$ | O | CH$_3$ | CH | |
| H | SO$_2$N(CH$_3$)(CH$_2$CH$_2$CH$_3$) | H | O | OCH$_3$ | CH | |
| H | SO$_2$N(CH$_2$CH$_3$)$_2$ | H | O | CH$_3$ | N | |
| H | SO$_2$N(CH$_2$CH$_2$CH$_3$)$_2$ | H | O | OCH$_3$ | N | |
| H | SO$_2$N(OCH$_3$)CH$_3$ | H | O | CH$_3$ | CH | |
| H | SCH$_3$ | H | O | OCH$_3$ | CH | |
| H | SCH$_2$CH$_3$ | H | O | CH$_3$ | N | |
| H | SCH$_2$CH$_2$CH$_3$ | H | O | OCH$_3$ | N | |
| H | SCH$_2$CH=CH$_2$ | H | O | CH$_3$ | CH | |
| H | S(O)CH$_3$ | 2-Cl | O | OCH$_3$ | CH | |
| H | S(O)CH$_2$CH$_3$ | H | O | CH$_3$ | N | |
| H | S(O)CH$_2$CH$_2$CH$_3$ | H | O | OCH$_3$ | N | |
| H | S(O)CH$_2$CH=CH$_2$ | H | O | CH$_3$ | CH | |
| H | SO$_2$CH$_3$ | H | O | CH$_3$ | CH | |
| H | SO$_2$CH$_3$ | H | O | OCH$_3$ | CH | |
| H | SO$_2$CH$_3$ | H | O | CH$_3$ | N | |
| H | SO$_2$CH$_3$ | H | O | OCH$_3$ | N | |
| H | SO$_2$CH$_2$CH$_3$ | H | O | CH$_3$ | CH | |
| H | SO$_2$CH$_2$CH$_3$ | H | O | OCH$_3$ | CH | |
| H | SO$_2$CH$_2$CH$_3$ | H | O | CH$_3$ | N | |
| H | SO$_2$CH$_2$CH$_3$ | H | O | OCH$_3$ | N | |
| H | SO$_2$CH$_2$CH$_2$CH$_3$ | H | O | CH$_3$ | CH | |
| H | SO$_2$CH$_2$CH=CH$_2$ | H | O | OCH$_3$ | CH | |
| H | CO$_2$CH$_3$ | H | O | CH$_3$ | CH | |
| H | CO$_2$CH$_3$ | H | O | OCH$_3$ | CH | |
| H | CO$_2$CH$_3$ | H | O | CH$_3$ | N | |
| H | CO$_2$CH$_3$ | H | O | OCH$_3$ | N | |
| H | CO$_2$CH$_2$CH$_3$ | H | O | CH$_3$ | CH | |
| H | CO$_2$CH$_2$CH$_3$ | H | O | OCH$_3$ | CH | |
| H | CO$_2$CH$_2$CH$_3$ | H | O | CH$_3$ | N | |
| H | CO$_2$CH$_2$CH$_3$ | H | O | OCH$_3$ | N | |
| H | CO$_2$CH$_2$CH$_2$CH$_3$ | H | O | CH$_3$ | CH | |
| H | CO$_2$CH(CH$_3$)$_2$ | 2-CH$_3$ | O | OCH$_3$ | CH | |
| H | CO$_2$CH$_2$CH=CH$_2$ | H | O | CH$_3$ | N | |
| H | CO$_2$CH$_2$C≡CH | H | O | OCH$_3$ | N | |
| H | CO$_2$CH$_2$CH$_2$Cl | H | O | CH$_3$ | CH | |
| H | CO$_2$CH$_2$CH$_2$OCH$_3$ | H | O | OCH$_3$ | CH | |
| H | CONHCH$_3$ | H | O | CH$_3$ | N | |
| H | CON(CH$_3$)CH$_2$CH$_3$ | H | O | OCH$_3$ | N | |
| H | CON(CH$_2$CH$_3$)$_2$ | H | O | CH$_3$ | CH | |
| H | CON(CH$_2$CH$_2$CH$_3$)(CH$_3$) | H | O | OCH$_3$ | CH | |
| H | CON(CH$_2$CH=CH$_2$)(CH$_3$) | H | O | CH$_3$ | N | |
| H | CHO | H | O | OCH$_3$ | N | |
| H | C(O)CH$_3$ | H | O | CH$_3$ | CH | |
| H | C(O)CH$_2$CH$_3$ | H | O | OCH$_3$ | N | |
| H | C(O)CH$_2$CH$_2$CH$_3$ | H | O | CH$_3$ | CH | |
| H | CF$_2$H | H | O | OCH$_3$ | CH | |
| H | CH$_2$CH$_2$F | H | O | CH$_3$ | N | |
| H | CCl$_3$ | H | O | OCH$_3$ | N | |
| H | CHClCH$_2$Cl | H | O | CH$_3$ | CH | |
| H | CH$_2$OCH$_3$ | H | O | OCH$_3$ | CH | |
| H | CH$_2$CH$_2$OCH$_2$CH$_3$ | H | O | CH$_3$ | N | |
| H | CH$_2$SCH$_2$CH$_3$ | H | O | OCH$_3$ | N | |
| H | CH$_2$CH$_2$SCH$_3$ | H | O | CH$_3$ | CH | |
| H | CH$_2$CN | H | O | OCH$_3$ | CH | |
| H | CH$_2$CH$_2$CN | H | O | CH$_3$ | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE IV

|  | Active | Weight Percent* | |
| --- | --- | --- | --- |
|  | Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 2

Wettable Powder

| | |
| --- | --- |
| 3-[[(4-cyclopropane-6-methoxy-1,3,5-triazin-2-yl)-aminocarbonyl]aminosulfonyl]-2-thiophenecarboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 3

Wettable Powder

| | |
| --- | --- |
| 3-[[(4-cyclopropane-6-methoxy-1,3,5-triazin-2-yl)-aminocarbonyl]aminosulfonyl]-2-thiophenecarboxylic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

Granule

| | |
| --- | --- |
| Wettable Powder of Example 3 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 5

Extruded Pellet

| | |
| --- | --- |
| 3-[[(4-cyclopropane-6-methoxy-1,3,5-triazin-2-yl)-aminocarbonyl]aminosulfonyl]-2-thiophenecarboxylic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

Oil Suspension

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 7

Wettable Powder

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 8

Low Strength Granule

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 9

Aqueous Suspension

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 10

Solution

| | |
|---|---|
| 3-[[(4-cyclopropane-6-methoxy-1,3,5-triazin-2-yl)-aminocarbonyl]aminosulfonyl]-2-thiophenecarboxylic acid, methyl ester, ammonium salt | 5% |
| water | 95% |

The salt is added directly to the water with stirring to produce the solution, which may then be packaged for use.

EXAMPLE 11

Low Strength Granule

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 12

Granule

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a flid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 13

High Strength Concentrate

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 14

Wettable Powder

| | |
|---|---|
| 3-[[(4-cyclopropane-6-methoxy-1,3,5-triazin-2-yl)- | 90% |

-continued

| | |
|---|---|
| aminocarbonyl]aminosulfonyl]-2-thiophenecarboxylic acid, methyl ester | |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 15

Wettable Powder

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 16

Oil Suspension

| | |
|---|---|
| 3-[](4-cyclopropane-6-methoxy-1,3,5-triazin-2-yl)-aminocarbonyl]aminosulfonyl]-2-thiophenecarboxylic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 17

Dust

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 18

Emulsifiable Concentrate

| | |
|---|---|
| 3-[[(4-cyclopropane-6-methoxy-1,3,5-triazin-2-yl)-aminocarbonyl]aminosulfonyl]-2-thiophenecarboxylic acid, methyl ester | 10% |
| chlorobenzene | 84% |
| sorbitan monostearate and polyoxyethylene condensates thereof | 6% |

The ingredients are combined and stirred to produce a solution which can be emulsified in water for application.

Utility

Test results indicate that the compounds of the present invention are highly active preemergent or postemergent herbicides or plant growth regulators. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops, such as rice and wheat. Alternatively, the subject compounds are useful to modify plant growth.

The rates of application for the compounds of the invention are determined by a number of factors, including their use as plant growth regulators or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

COMPOUNDS

COMPOUNDS

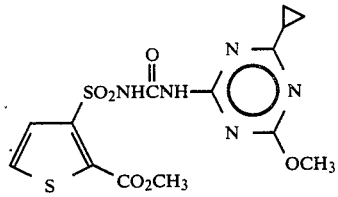

Compound 1

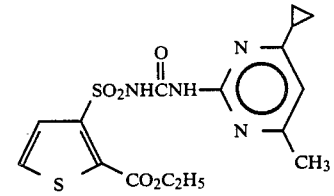

Compound 2

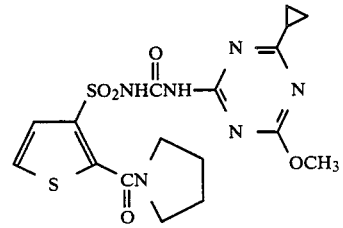

Compound 3

-continued
COMPOUNDS

Compound 4

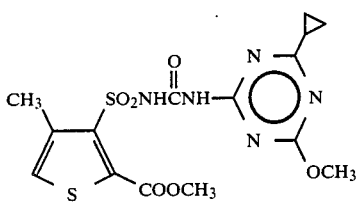

Compound 5

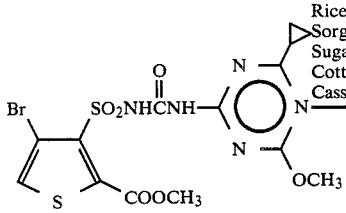

Test A

Seeds of crabgrass (Digitaria spp.), barnyardgrass (Echinochloa crusgalli), wild oats (Avena fatua), morningglory (Ipomoea spp.), cocklebur (Xanthium pensylvanicum), sicklepod (Cassia obtusifolia), sorghum, corn, soybean, sugarbeet, cotton, rice, wheat and purple nutsedge (Cyperus rotundus) tubers were planted and treated preemergence with the test chemicals dissolved in a nonphytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

TABLE A

|  | Compound 1 | Compound 2 | | Cmpd. 3 | Cmpd. 4 | | Cmpd. 5 |
| --- | --- | --- | --- | --- | --- | --- | --- |
| Rate (kg/ha) | 0.1 | 0.05 | 0.01 | 0.05 | 0.05 | 0.01 | 0.01 |
| POST-EMERGENCE | | | | | | | |
| Morningglory | 5C,9G | 3C,9H | 1H | 4C,9G | 10C | 10C | 3C,7G |
| Cocklebur | 9C | 2G | 2G | 5C,9G | 9C | 2C,8H | 10C |
| Velvetleaf |  | 4C,9G | 1C,6G | 2C,4G | 10C | 10C | 10C |
| Nutsedge | 3G | 3C,8G | 2C,8G | 3G | 5G | 0 | 0 |
| Crabgrass | 0 | 2G | 0 | 0 | 0 | 0 | 0 |
| Giant Foxtail |  | 5G | 0 | — | 3C,6G | 2G | 0 |
| Barnyardgrass | 0 | 0 | 0 | 0 | 3C,8H | 2C,5H | 0 |
| Cheatgrass |  | 5G | 0 | 0 | 2C,8G | 0 | 0 |
| Wild Oats | 0 | 0 | 0 | 0 | 3C,8G | 3G | 0 |
| Wheat | 0 | 0 | 0 | 0 | 9G | 4G | 0 |
| Corn | 3G | 2C,6H | 1C | 2C,8H | 2G | 0 | 0 |
| Barley |  | 0 | 0 | — | 3C,9G | 3C,7G | 0 |
| Soybean | 3C,8G | 2C | 0 | 4G | 5C,9G | 4C,9H | 0 |
| Rice | 0 | 2C | 1C | 4G | 9G | 4G | 0 |
| Sorghum | 2G | 2C,7H | 1C,5G | 2C,8H | 3C,9H | 7H | 0 |
| Sugar beets | 9C | 1C,6G | 5G | 3C,8G | 9C | 10C | 9C |
| Cotton | 4C,9G | 2C,8H | 2C,7G | 3C,8G | 10C | 9G | 10C |
| Cassia | 0 | — | — | — | — | — | — |
| PRE-EMERGENCE | | | | | | | |
| Morningglory | 3C,9G | 0 | — | 2C,3H | 9H | 8G | 0 |
| Cocklebur | 9H | 5G | — | 3C,4G | 2C,6H | 0 | 0 |
| Velvetleaf |  | 1C | 4G | 2C,4G | 2C,8H | 0 | 0 |
| Nutsedge | 3G | 0 | — | 3G | 0 | 0 | 0 |
| Crabgrass | 0 | 0 | — | 0 | 0 | 0 | 0 |
| Giant Foxtail |  | 7G | — | — | 8G | 0 | 0 |
| Barnyardgrass | 0 | 0 | — | 0 | 5H | 0 | 0 |
| Cheatgrass |  | 2G | — | 0 | 6G | 4G | 0 |
| Wild Oats | 0 | 0 | — | 0 | 5G | 0 | 0 |
| Wheat | 0 | 0 | — | 0 | 7G | 0 | 0 |
| Corn | 7G | 2C | 3G | 2C | 0 | 0 | 0 |
| Barley |  | 0 | — | — | 2C,5G | 0 | 0 |
| Soybean | 1C,3H | 0 | — | 1C | 6H | 2H | 0 |
| Rice | 3G | 0 | — | 0 | 9H | 6G | 0 |
| Sorghum | 2G | 2C | 6H | 2C,5G | 3C,9H | 2C,2G | 0 |
| Sugar beets | 9C | 1C | 4G | 3C,8G | 4C,9G | 8G | 0 |
| Cotton | 9G | 0 | — | 0 | 7G | 0 | 0 |
| Cassia | 4G | — | — | — | — | — | — |

Test B

Postemergence

Two round pans (25 cm diameter by 12.5 cm deep) were filled with Sassafras sandy loam soil. One pan was planted with blackgrass (Alopecurus myosuroides), sugar beets, nutsedge (Cyperus rotundus) tubers, crabgrass (Digitaria sanquinalis), sicklepod (Cassia obtusifolia), teaweed (Sida spinosa), jimsonweed (Datura stramonium), velvetleaf (Abutilon theophrasti), giant foxtail (Setaria faberii) and rape (Brassica napus). The other pan was planted with wheat, cotton, rice, corn, soybean, wild oats (Avena fatua), cocklebur (Xanthium pensylvanicum), morningglory (Ipomoea hederacea), johnsongrass (Sorghum halepense) and barnyardgrass (Echinochloa crusgalli). The plants were grown for approximately fourteen days, then sprayed postemergence with the chemicals dissolved in a nonphytotoxic solvent.

Preemergence

Two round pans (25 cm diameter by 12.5 cm deep) were filled with Sassafras sandy loam soil. One pan was planted with blackgrass, sugar beets, nutsedge, crabgrass, sicklepod, teaweed, jimsonweed, velvetleaf, giant foxtail and rape. The other pan was planted with wheat, cotton, rice, corn, soybeans, wild oats, cocklebur, morningglory, johnsongrass, and barnyardgrass. The two pans were sprayed preemergence with the chemicals dissolved in a nonphytotoxic solvent.

Treated plants and controls were maintained in the greenhouse for 28 days, then all treated plants were compared to controls and visually rated for plant response.

Response ratings are based on a scale of 0 to 10: where 0=no effect, and 10=complete control. The type of response is indicated by letters where G=growth retardation and C=chlorosis/necrosis.

TABLE B

| | Compound 1 | | | |
|---|---|---|---|---|
| Rate (g/ha) | 250 | 62 | 16 | 4 |
| POST-EMERGENCE | | | | |
| Corn | 2G | 0 | 0 | 0 |
| Wheat | 0 | 0 | 0 | 0 |
| Rice | 3G | 0 | 0 | 0 |
| Soybean | 3G | 0 | 0 | 0 |
| Cotton | 10G | 10G | 7G | 3G |
| Sugar beet | 10C | 10C | 10C | 10C |
| Crabgrass | 3G | 0 | 0 | 0 |
| Johnsongrass | 0 | 0 | 0 | 0 |
| Blackgrass | 3G | 0 | 0 | 0 |
| Barnyardgrass | 0 | 0 | 0 | 0 |
| Nutsedge | 6C | 3C | 0 | 0 |
| Giant Foxtail | — | — | — | — |
| Wild Oats | 0 | 0 | 0 | 0 |
| Cocklebur | 10G | 10G | 7G | 4G |
| Morningglory | 10G | 9G | 7G | 3G |
| Teaweed | 8G | 5G | 3G | 0 |
| Cassia | 3G | 0 | 0 | 0 |
| Jimsonweed | 9G | 9G | 4G | 0 |
| Velvetleaf | 10G | 10G | 9G | 4G |
| PRE-EMERGENCE | | | | |
| Corn | 4G | 2G | 0 | 0 |
| Wheat | 0 | 0 | 0 | 0 |
| Rice | 8G | 6G | 4G | 3G |
| Soybean | 0 | 0 | 0 | 0 |
| Cotton | 7G | 5G | 2G | 0 |
| Sugar beet | 9G | 9G | 6G | 3G |
| Crabgrass | 4G | 3G | 0 | 0 |
| Johnsongrass | 3G | 0 | 0 | 0 |
| Blackgrass | 6G | 4G | 0 | 0 |
| Barnyardgrass | 0 | 0 | 0 | 0 |
| Nutsedge | 4G | 0 | 0 | 0 |
| Giant Foxtail | 2G | 0 | 0 | 0 |
| Wild Oats | 0 | 0 | 0 | 0 |
| Cocklebur | 7G | 5G | 3G | 0 |
| Morningglory | 6G | 2G | 0 | 0 |
| Teaweed | 8G | 6G | 3G | 0 |
| Cassia | 9G | 7G | 5G | 3G |
| Jimsonweed | 9G | 8G | 5G | 0 |
| Velvetleaf | 9G | 6G | 3G | 0 |

What is claimed is:

1. A compound of the formula:

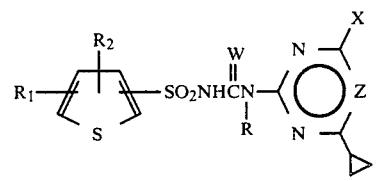

wherein
W is O or S;
R is H or $CH_3$
$R_1$ is H, $C_1$-$C_4$ alkyl, $CH_2CH=CH_2$, $CF=CFCF_3$, $C_1$-$C_2$ alkoxy, $NO_2$, Cl, Br, $SO_2NR_3R_4$, $SO_2N(OCH_3)CH_3$, $S(O)_nR_5$, $CO_2R_6$, $C(O)NR_7R_8$, $C(O)R_9$ or $C_1$-$C_2$ alkyl substituted with F, Cl, $C_1$-$C_2$ alkoxy, $C_1$-$C_2$ alkylthio or CN;
$R_2$ is H, Cl, F, Br, $C_1$-$C_2$ alkyl, $C_1$-$C_2$ alkoxy, $S(O)_nR_{10}$, $C_1$-$C_2$ haloalkyl, CN, $C_2$-$C_3$ cyanoalkyl, $CH_2OCH_3$, $CH_2SCH_3$ or $CH_2CH_2OCH_3$;
$R_3$ and $R_4$ are independently $C_1$-$C_3$ alkyl;
$R_3$ and $R_4$ may be taken together as $(CH_2)_4$, $(CH_2)_5$ or $CH_2CH_2OCH_2CH_2$;
$R_5$ is $C_1$-$C_3$ alkyl or $CH_2CH=CH_2$;
$R_6$ is $C_1$-$C_3$ alkyl, $CH_2CH=CH_2$, $CH_2C\equiv CH$, $CH_2CH_2Cl$ or $CH_2CH_2OCH_3$;
$R_7$ is $C_1$-$C_3$ alkyl;
$R_8$ is H, $C_1$-$C_3$ alkyl or $CH_2CH=CH_2$;
$R_9$ is H or $C_1$-$C_3$ alkyl;
$R_{10}$ is $C_1$-$C_2$ alkyl;
n is 0, 1 or 2;
X is $CH_3$, $OCH_3$, $OCH_2CH_3$, or $CH_2OCH_3$; and
Z is N;
and their agriculturally suitable salts; provided that $R_1$ and the sulfonylurea bridge are on adjacent carbon atoms of the thiophene ring.

2. A compound according to claim 1 where
W is O;
R is H;
$R_1$ is H, $C_1$-$C_2$ alkyl, $CF=CFCF_3$, Cl, Br, $SO_2N(CH_3)_2$, $SO_2(C_1$-$C_2$ alkyl) or $CO_2(C_1$-$C_2$ alkyl);
$R_2$ is H, F, Br, Cl, $CH_3$, $S(O)_nCH_3$, or $CH_2OCH_3$; and
X is $CH_3$ or $OCH_3$.

3. The compound of claim 1 which is 3-[[(4-cyclopropane-6-methoxy-1,3,5-triazin-2-yl)aminocarbonyl]aminosulfonyl]-2-thiophenecarboxylic acid, methyl ester.

4. A composition suitable for controlling the growth of undesired vegetation which comprises an effective amount of a compound of claim 1 and at least one of the following: surfactant, solid or liquid diluent.

5. A composition suitable for controlling the growth of undesired vegetation which comprises an effective amount of a compound of claim 2 and at least one of the following: surfactant, solid or liquid diluent.

6. A composition suitable for controlling the growth of undesired vegetation which comprises an effective amount of a compound of claim 3 and at least one of the following: surfactant, solid or liquid diluent.

7. A method for controlling the growth of undesired vegetation which comprises applying to the locus to be protected an effective amount of a compound of claim 1.

8. A method for controlling the growth of undesired vegetation which comprises applying to the locus to be protected an effective amount of a compound of claim 2.

9. A method for controlling the growth of undesired vegetation which comprises applying to the locus to be protected an effective amount of a compound of claim 3.

* * * * *